United States Patent [19]

Robinson

[11] 4,059,630

[45] Nov. 22, 1977

[54] ANTI-ANDROGENIC STEROIDS

[75] Inventor: Cecil H. Robinson, Pylesville, Md.

[73] Assignee: The Johns Hopkins University, Baltimore, Md.

[21] Appl. No.: 661,792

[22] Filed: Feb. 26, 1976

[51] Int. Cl.$^2$ .............................................. C07C 49/45
[52] U.S. Cl. .............................. 260/586 E; 424/311; 424/331; 560/256
[58] Field of Search ......................... 260/586 E, 488 B

[56] References Cited

PUBLICATIONS

Federation Proceedings, vol. 34, No. 3, (Mar. 1, 1975), Batzold & Robinson.
Batzold & Robinson, J.A.C.S., vol. 97, p. 2576, (1975).
Batzold & Robinson, J. Org. Chem. 41, 313, (1976).
Carrell et al., American Crystallographic Assoc. Winter Meeting, Jan. 19, 1976, Clemson Univ., S. Carolina.

*Primary Examiner*—Gerald A. Schwartz
*Attorney, Agent, or Firm*—Cushman, Darby & Cushman

[57] ABSTRACT

The present invention relates to certain new and useful steroids which demonstrate anti-androgenic properties. These steroids are 5,10-secosteroids that have been found to be potent irreversible inhibitors of the enzyme $\Delta^5$-3-ketosteroid isomerase which is involved in androgen biosynthesis. In addition, certain of the steroids of the invention compete reversibly with 5-α-dihydrotestosterone for binding to the prostatic cytoplasmic receptor protein while others inhibit the enzyme prostatic testosterone 5-α-reductase. The anti-androgenic properties of the present compounds indicate such utility as the control of abnormal growth of the human prostate, e.g. in the therapy of human prostatic cancer.

3 Claims, No Drawings

ANTI-ANDROGENIC STEROIDS

The invention described herein was made in the course of work under a grant or award from the Department of Health, Education and Welfare.

BACKGROUND OF THE INVENTION

Prior studies[1] have shown that remarkably specific irreversible enzyme inhibitors can result from compounds bearing potential reactive groupings which are unmasked at the active site by the target enzyme. This specificity resides in the generation of the alkylating agent by the target enzyme at the active site as a result of the enzyme's normal catalytic process. The process is exemplified by the enzymatic conversion of an acetylenic compound to an allene which can alkylate an active site amino acid residue. The first such example was provided by Bloch[2] who showed that the acetylenic analog of a normal substrate for $\beta$-hydroxydecanoyl thioester dehydrase is converted by the enzyme to the corresponding conjugated allenic thioester with rapid alkylation of an active site histidine residue. This approach has been applied to the inhibition of monoamine oxidase[3] and $\gamma$-cystathionase.[4]

1. Cf. R. R. Rando, Science, 185, 320 (1974).
2. K. Bloch, Acc. Chem. Res. 2, 193 (1969); K. Endo, G. M. Helmkamp, and K. Bloch, J. Biol. Chem. 245, 4293 (1970); M. Morisaka and K. Bloch, Bioorg. Chem., 1 188 (1971).
3. R. R. Rando, J. Am. Chem. Soc., 95, 4438 (1973); R. R. Rando and J. De Mairena, Biochem. Pharmacol., 23, 463 (1974); R. C. Hevey, J. Babson, A. L. Maycock, and R. H. Abeles, J. Am. Chem. Soc., 95, 6125 (1973).
4. R. H. Abeles and C. T. Walsh, J. Am. Chem. Soc. 95, 6124 (1973).

The enzyme $\Delta^5$-3-ketosteroid isomerase[5] (EC 5.3.3.1) from *Pseudomonas testosteroni* converts $C_{19}$ and $C_{21}$ $\Delta^5$-3-ketosteroids to the corresponding $\Delta^4$-3-ketosteroids. The proposed mechanism[5,6] involves removal of the axial $4\beta$-hydrogen with concomitant enolization to give a $\Delta^{3,5}$-dienol, followed by ketonization with axial reprotonation at C-6. The hydrogen transfer from C-4 to C-6 is intramolecular. See Scheme 1 below:

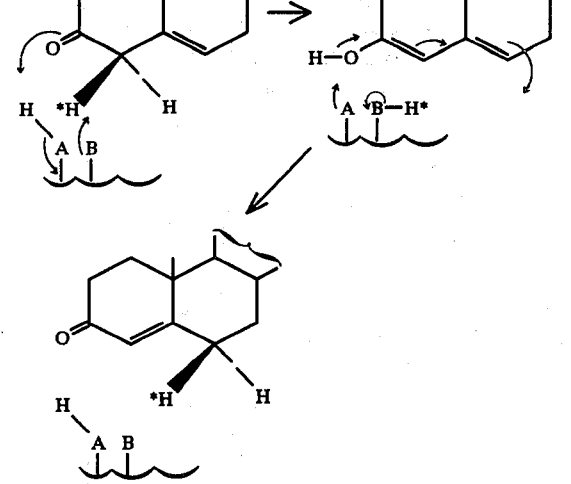

5. P. Talalay and A. M. Benson, Enzymes, 6, 591 (1972).
6. S. K. Malhotra and H. J. Ringold, J. Am. Chem. Soc., 87, 3228 (1965). The indicated reaction, when carried out by mammalian $\Delta^5$-3-ketosteroid isomerases is a key step in the biosynthesis of steroid hormones.

SUMMARY OF THE INVENTION

The present invention is based on the finding that there is rapid irreversible inhibition of bacterial $\Delta^5$-3-ketosteroid isomerase by certain novel acetylenic steroid analogs (illustrated by 1 and 2) (Scheme II).

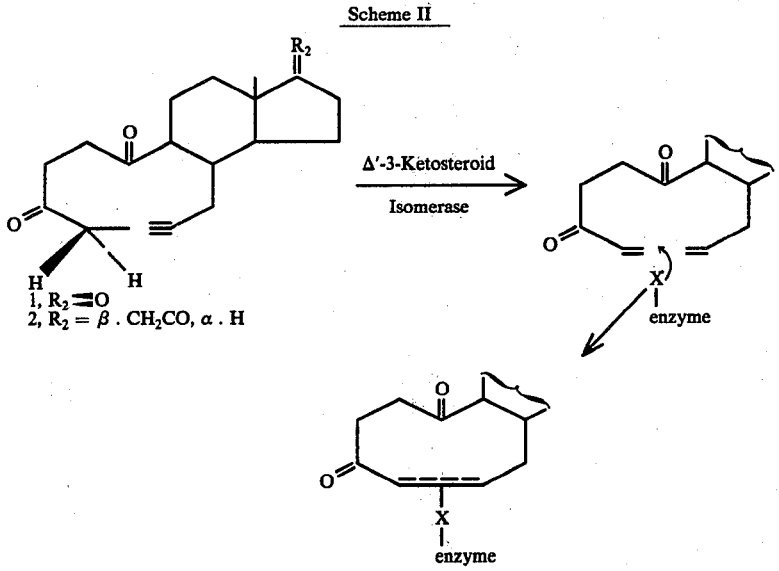

Compounds 1 and 2 above are, respectively, 5,10-seco-estr-5-yne-3,10,17-trione and 5,10-seco-19-norpregn-5-yne-3,10,20-trione. For convenience, these compounds are referred to herein as compounds 1 and 2 or as "estryne" or "pregnyne", respectively.

It appears that the inhibition of bacterial $\Delta^5$-3-ketosteroid isomerase by compounds 1 and 2, or by other acetylenic steroids within the scope of this invention, involves conversion of the $\beta,\gamma$-acetylenic ketone to the conjugated allenic ketone via enzymatic enolization followed by ketonization at C-3 with protonation at C-6. The conjugated allenic ketones, which are also novel and constitute another embodiment of the invention, then react readily with a nucleophilic residue at or near the active site. This process finds analogy in studies with β-hydroxydecanoyl thioester dehydrase.

While compounds (1) and (2) above (estryne and pregnyne, respectively) are preferred compounds, the invention is of broader scope and extends to acetylenic steroids of the following structure A:

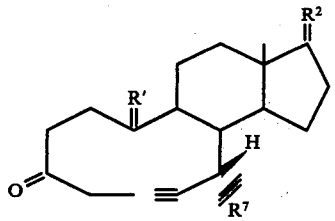

wherein R¹ stands for CH$_2$=, O= or

R² is O=,

(where R³ is H or lower alkanoyl);

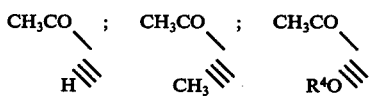

(where R⁴ is H or lower alkanoyl);

(where R⁵ is lower alkyl) or

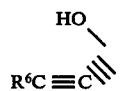

(where R⁶ is H, lower alkyl or Cl); and R⁷ is H or CH$_3$.

Correspondingly, the allenic steroids of the invention are shown by structures B and C:

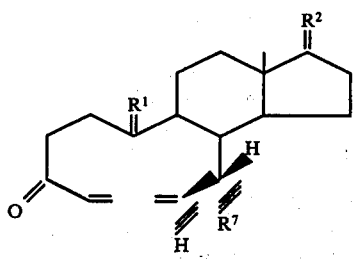

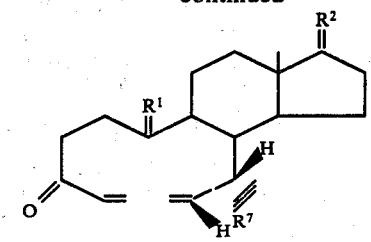

wherein R¹, R² and R⁷ have the meanings given above.

As indicated, preferred compounds of structure A are 5,10-secoestr-5-yne-3,10,17-trione and 5,10-seco-19-nor-pregn-5-yne-3,10-20-trione, i.e. compounds 1 and 2, Scheme 2 above. These compounds may be synthesized by closely similar routes. Thus, 3β,17β-diacetoxyestr-5(10)-en-6-one (3) may be prepared by direct chromium trioxidepyridine oxidation of 3β,17β-diacetoxyandrost-5-en-19-ol (cf. U.S. Pat. Nos. 3,159,621 and 3,261,830). Epoxidation of (3) with m-chloroperbenzoic acid in benzene (reflux) or by reaction with alkaline hydrogen peroxide followed by reacetylation gives the corresponding 5β-10β-oxidosteroid (4), mp 245°-247°. Fragmentation of (4) with p-toluene sulfonylhydrazine[6'] at ambient temperature in acetic acidchloroform (1:1) gives 3β,17β-diacetoxy-5,10-secoestr-5-yn-10-one (5), mp 204°-206°, in high yield. Hydrolysis of the acetate groups in (5) (3% methanolic KOH) followed by oxidation with Jones reagent[7] gives (1). Compound (2) may be synthesized by exactly the same sequence of reactions starting with 3β, 20-diacetoxy-5-pregnen-19-ol.

[6'.] M. Tanabe, D. F. Crowe, and R. L. Dehn, Tetrahedron Lett., 3943 (1967); A. Eschenmoser, D. Felix, and G. Ohloff, Helv. Chim. Acta, 50, 708 (1967).

[7.] K. Bowden, I. M. Heilbron, E. R. H. Jones, and C. B. L. Weedon, J. Chem. Soc., 39 (1946).

Incubation of crystalline Δ⁵-ketosteroid isomerase at pH 7.0 with acetylenic steroids (1) and (2) in 1,4-dioxane results in rapid irreversible and complete inactivation of the enzyme. The inactivation is progressive with time, and half-lives in the range of 150-1320 sec are observed at concentrations of 20-200 μM of the two inhibitors. The enzymatic activities of control vessels which received only equivalent volumes of 1,4-dioxane remained constant at initial activities. Evidence for the irreversible nature of the inhibition is based on: inability to restore enzymatic activity by prolonged dialysis (24 hr at 4° vs. 1 mM potassium phosphate buffer, pH 7.0); the fact that extensively diluted partially inhibited enzyme preparations retain constant activity for many days; and the kinetic behavior described below.

The initial rates of inactivation of the isomerase by (1) and (2) can be analyzed by the method of Kitz and Wilson[8] since very satisfactory pseudo-first-order behavior was observed. It is assumed that [I] (inhibitor) >> [E] (enzyme), that [E.I] (the reversible enzyme-inhibitor complex) is at all times in equilibrium with enzyme and inhibitor, and that $k_{cat} >> k_{inh}$. The scheme for the formation of EI' (the irreversible enzyme-inhibitor derivative) may then be represented as follows.

[8.] R. Kitz and I. B. Wilson, J. Biol. Chem., 237, 3245 (1964).

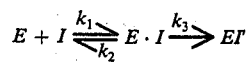

If the enzyme-inhibitor solution is diluted extensively prior to assay, the active enzyme (ε) = [E] + [E.I].

Then $-d(\epsilon)/dt = k_3[E.I]$, and $K_1 = ([E][I])/[EI]$. Thus $$\ln\frac{(\epsilon)}{[E_t]} = \frac{-k_3}{1 + (K_1/[I])}$$

where $E_t$ = total amount of enzyme in system.
If one defines $$k_{app} = \frac{-k_3}{1 + (K_1/[I])}$$

then $$\frac{1}{k_{app}} = \frac{1}{k_3} + \frac{K_1}{K_3[I]}$$

Consequently double reciprocal plots of $k_{app}$ with respect to [I] should be linear, with slopes and intercepts permitting the determination of $K_1$ and $k_3$ where the latter is the overall rate constant for the irreversible inhibition process.

From plots of ln $\epsilon$ (residual enzymatic activity) vs. time, $k_{app}$ has been determined at five inhibitor concentrations for both compounds 1 and 2, i.e. estryne and pregnyne. Strict linearity of the semilogarithmic plots has been observed in all cases, over greater than two half-lives. A plot of $1/k_{app}$ vs. $1/[I]$ was linear and gave $k_3$ and $K_1$ (FIG. 1). For compound 1, $K_1 = 56\mu M$ and $k_3 = 1.98 \times 10^{-3} sec^{-1}$, and for compound 2, $K_1 = 32\mu M$ and $k_3 = 4.10 \times 10^{-3} sec^{-1}$.

These experiments indicate that the acetylenic steroids (1) and (2) inactivate $\Delta^5$-3-ketosteroid isomerase by covalent linkage to the enzyme. The inactivation is rapid and specific, presumably because the isomerase enzyme generates the alkylating system at its active site by exercising its normal catalytic function.

DETAILED DESCRIPTION OF PREFERRED EMBODIMENTS

The following examples illustrate the preparation of the preferred compounds (1) and (2) above.

EXAMPLE 1

3β,17β-Diacetoxyestr-5(10)-en-6-one

A solution of 3β,17β-diacetoxy-19-hydroxy androst-5-ene (20g) in pyridine (80ml) is added in one portion to a stirred mixture of chromium trioxide (40g) and pyridine (400ml) at 25°. The reaction mixture is stirred at 25° for 96 hours, and is then diluted with ether (1200ml) and then is filtered through Celite. The residue on the filter is washed with ether and the combined filtrate and washings are washed successively with 5% aqueous sodium hydroxide, water, 10% aqueous hydrochloric acid, water, then dried ($Na_2SO_4$) and evaporated to dryness. The residue is subjected to dry column chromatography on silica gel, eluting with chloroform-ethyl acetate (15:1) and there results the compound of this Example (1), mp 123°–124° (after crystallization from acetone-petroleum ether; mass spectrum m/e 374(M+), 332, 314, 286.

EXAMPLE 2

3β,17β-Diacetoxy-5β,10β-oxidoestran-6-one

To a solution of 3β,17β-diacetoxyestr-5(10)-en-6-one (10.2g) in benzene (820ml) is added m-chloro perbenzoic acid (15.7g) and the solution is heated under reflux for 1 hour. The reaction mixture is then cooled, washed successively with water, 5% aqueous sodium bicarbonate solution and water, is dried ($Na_2SO_4$) and evaporated in vacuo to give a solid residue. Crystallization from methylene chloride-acetone gives the compound of this Example (2) mp 245°–247°; mass spectrum, m/e 390(M+), 330, 314, 302, 286.

EXAMPLE 3

3β,17β-Diacetoxy-5,10-secoestr-5-yn-10-one

To a stirred solution of 3β,17β-diacetoxy-5β,10β-oxidoestran-6-one (6.0g) in a mixture of chloroform (100ml) at 25° is added p-toluene sulfonyl hydrazine (1.24g). Stirring is continued for 6 hours at 25°, and the reaction mixture is then diluted with water and extracted with chloroform. The chloroform extract is then washed successively with water, 5% aqueous sodium bicarbonate solution and water, and is dried ($Na_2SO_4$) and evaporated in vacuo to give a solid residue. This residue is crystallized from methanol to give the compound of this Example (3) (1.7g) as plates mp 204°–206°; mass spectrum m/e 374(M+), 332, 316, 304, 286.

EXAMPLE 4

3β,17β-Dihydroxy-5,10-secoestr-5-yn-10-one

3β,17β-dihydroxy-5,10-secoestr-5-yn-10-one (374mg) is dissolved in 3% methanolic potassium hydroxide (75ml) and the solution is stirred at 25° for three hours. The reaction mixture is then evaporated in vacuo at 30° to about 10ml, and saturated aqueous sodium chloride solution (40ml) is added. The resulting mixture is extracted with chloroform, and the chloroform extract is washed with water, dried ($Na_2SO_4$) and evaporated in vacuo to give the compound of this Example (4), mp 207°–208°; mass spectrum m/e 290(M+), 272, 262, 254, 244.

EXAMPLE 5

5,10-Secoestr-5-yne-3,10,17-trione ("Estryne")

To a solution of 3β,17β-dihydroxy-5,10-secoestr-5-yn-10-one (4; 1.0g) in acetone (150ml) at 5° is added, dropwise, Jones' reagent (chromium trioxide in sulfuric acid-water) until a permanent orange-brown coloration persists. After 5 minutes at 5°, the mixture is treated with methanol to destroy excess chromic acid and is diluted with water and extracted with ether. The ethereal extract is washed with water, dried ($Na_2SO_4$) and evaporated to give a solid residue. Crystallization from acetone-petroleum ether gives the compound of this Example (5), mp 142°–145°; mass spectrum m/e 286(M+), 271, 258, 243, 230, 215.

EXAMPLE 6

3β,20β-Diacetoxy-19-norpregn-5(10)-en-6-one

A solution of 3β,20β-diacetoxy-19-hydroxypregn-5-ene (32g) in pyridine (120ml) is added in one portion to a stirred mixture of chromium trioxide (60g) and pyridine (600ml) at 25°. The reaction mixture is stirred at 25° for 96 hours and is diluted with ether (1800ml) and then is filtered through Celite. The residue on the filter is washed with ether, and the combined filtrate and washings are washed successively with 5% aqueous sodium hydroxide, water, 10% aqueous hydrochloric acid, water, then dried ($Na_2SO_4$) and evaporated to dryness. The residue is subjected to dry column chromatography or silica gel, eluting with chloroform-ethyl acetate (15:1) and there results the compound of this Example (6), mp 144°–148°; λ$_{max}^{MeOH}$ 248 nm (E=10,400).

EXAMPLE 7

3β,20β-Diacetoxy-5β,10β-oxido-19-norpregnan-6-one

To a solution of 3β,20β-diacetoxy-19-norpregn-5(10)-en-6-one (5g) in benzene (400ml) is added m-chloroperbenzoic acid (8g) and the solution is heated under reflux for one hour. The reaction mixture is then cooled, washed successively with water, 5% aqueous sodium bicarbonate solution and water, is dried (Na$_2$SO$_4$) and evaporated in vacuo to give a solid residue. Crystallization from hexane-ethanol gives the compound of this Example (7), mp. 134°–136°; mass spectrum, m/e 418, 360, 358, 342, 340, 330.

EXAMPLE 8

3β,20β-Diacetoxy-5,10-seco-19-norpregn-5-yn-10-one

To a stirred solution of 3β,20β-diacetoxy-5β,10β-oxido-19-norpregnan-6-one (9g) in a mixture of chloroform (150ml) and glacial acetic acid (150ml) at 25° is added p-toluene sulfonyl hydrazine (1.9g). Stirring is continued for 6 hours at 25°, and the reaction mixture is then diluted with water and extracted with chloroform. The chloroform extract is then washed successively with water, 5% aqueous sodium bicarbonate solution and water, and is dried (Na$_2$SO$_4$) and evaporated in vacuo to give a solid residue. This residue is crystallized from acetone-hexane to give the compound of this Example (8), mp. 132°–134°; mass spectrum m/e 402(M+), 360, 342, 282.

EXAMPLE 9

3β,20β-Dihydroxy-5,10-seco-19-norpregn-5-yn-10-one

3β,20β-diacetoxy-5,10-secoestr-5-yn-10-one (1.0g) is dissolved in 3% methanolic potassium hydroxide (150ml) and the solution is heated under reflux for 3 hours. The reaction mixture is cooled, evaporated in vacuo at 30° to about 20 ml and saturated aqueous sodium chloride solution (80ml) is added. The resulting mixture is extracted with chloroform, and the chloroform extract is washed with water, dried (Na$_2$SO$_4$) and evaporated in vacuo to give the compound of this Example (9), mp. 187°–188°; mass spectrum m/e 318(M+), 300, 285, 282, 272.

EXAMPLE 10

5,10-Seco-19-norpregn-5-yne-3,10,20-trione ("Pregnyne")

To a solution of 3β,20β-dihydroxy-5,10-seco-19-norpregn-5-yn-10-one (1.0g) in acetone (150ml) at 5° is added, dropwise, Jones' reagent (chromium trioxide in sulfuric acid-water) until a permanent orange-brown coloration persists. After 5 minutes at 5° methanol is added to the mixture to destroy excess chromic acid, and the mixture is then diluted with water and extracted with ether. The ethereal extract is washed with water, dried (Na$_2$SO$_4$) and evaporated to give a solid residue. Crystallization from acetone-petroleum ether gives the compound of this Example (10), mp. 156°–159°; mass spectrum m/e 314(M+), 286, 271.

Other examples include 5,10-seco-androst-5-yn-10(19)-ene-3,17-dione and 5,10-seco-pregn-5-yn-10(19)-ene-3,20-dione. The synthetic routes to these compounds are exactly analogous to each other and are illustrative of the preparation of those compounds of structure A, where R$^1$ = CH$_2$.

EXAMPLE 11

19-p-Toluenesulfonyloxy-3β,17β-diacetoxyandrost-5-ene

To a solution of 3β,17β-diacetoxy-19-hydroxyandrost-5-ene (14.4g) in pyridine (370ml) at 25° is added p-toluenesulfonyl chloride (38.1g) and the solution is left at 25° for 4 days. Water is then added, and the mixture is extracted with ethyl acetate, and the organic extract is washed successively with water, 5% aqueous hydrochloric acid, 5% aqueous sodium bicarbonate and water, and then dried (Na$_2$SO$_4$) and evaporated in vacuo. The residue is crystallized from methylene chloride-hexane to give the compound of this Example (11), mp. 135°–137°; mass spectrum m/e 484, 372, 312.

EXAMPLE 12

3β,17β-Diacetoxy-6β-hydroxy-5β,19-cycloandrostane

A solution of 19-p-toluenesulfonyloxy-3β,17β-diacetoxy androst-5-ene (15.0g) and potassium acetate (11.76g) in acetone-water (3:1; 750ml) is heated under reflux for 48 hours. The acetone is then removed in vacuo and the resulting aqueous mixture is extracted with ethyl acetate. The organic extract is washed with water, dried (Na$_2$SO$_4$) and evaporated in vacuo to give the crude product which is chromatographed on silica gel (eluant: chloroform-ethyl acetate, 9:1) to give the compound of this Example (12) as an oil, mass spectrum m/e 390(M+), 372, 330, 312, 270.

EXAMPLE 13

3β,17β-Diacetoxy-5β,19-cycloandrostan-6-one

A solution of 3β,17β-diacetoxy-6β-hydroxy-5β,19-cycloandrostane (1.3g) in acetone (100ml) at 5° is treated with Jones' reagent (CrO$_3$—H$_2$SO$_4$) until a permanent brown coloration persists. After 5 minutes at 5°, the mixture is concentrated in vacuo to about 20ml and is diluted with water. The aqueous mixture is extracted with ethyl acetate, washed with water, dried (Na$_2$SO$_4$) and evaporated in vacuo to give a solid residue. Crystallization from methylene chloride-hexane gives the compound of this Example (13), mp. 151°–152°, mass spectrum m/e 328, 313, 300, 268, 253, 225.

EXAMPLE 14

3β,17β-Diacetoxy-5β,19-cycloandrostan-6-one-p-toluenesulfonylhydrazine

To a solution of p-toluenesulfonylhydrazine (205mg) is methanol (10ml) is added 3β,17β-diacetoxy-5β,19-cycloandrostan-6-one (388mg) and the mixture is left at 25° for 24 hours. The reaction mixture is then filtered, and the residue on the filter is the pure compound of this Example (14), mp 288°–290°.

EXAMPLE 15

3β,17β-Diacetoxy-5,10-secoandrost-5-yn-10(19)-ene

A mixture of 3β,17β-diacetoxy-5β,19-cycloandrostan-6-one p-toluenesulfonylhydrazine (2.78g) and sodium hydride (150mg; added as dispersion in mineral oil) is suspended in o-xylene (200ml), and heated under reflux for 3 hours. The reaction mixture is then cooled, washed successively with 5% aqueous sodium bicarbonate and water, dried (Na$_2$SO$_4$) and evaporated to give a residue comprising substantially the compound of this Example (15), mass spectrum m/e 372(M+), 330, 312, 297, 252.

EXAMPLE 16

5,10-Secoandrost-5-yn-10(19)-ene-3,17-dione

The product of Example (15) is converted to a mixture containing the compound of this Example (16) by basic hydrolysis to give the 3β,17β-diol and oxidation of the 3β,17β-diol by Jones' reagent, according to the procedures of Examples (4) and (5) above.

EXAMPLE 17

The enzyme inhibitory properties of the compounds of this invention are illustrated by the following data obtained with the preferred compounds of the invention, i.e. compounds (1) and (2) (i.e. the "Estryne" and "Pregnyne" products of Examples (5) and (10), respectively).

Studies were performed using crystalline purified bacterial Δ$^5$-3-ketosteroid isomerase (from P. testosteroni), under pseudo first order conditions using the kinetic analysis of R. Kitz and I. B. Wilson [J. Biol. Chem., 237, 3245 (1964)]. Powerful irreversible inhibition of the enzyme was demonstrated thereby, with $K_I$ = 56 μM and $k_3$ = 1.98 × 10$^{-3}$ sec. $^{-1}$ for compound (1) and $K_I$ = 32 μM and $k_3$ = 4.1 × 10$^{-3}$ sec.$^{-1}$ for compound (2) (10-fold range of inhibitor concentrations).

In Vivo Properties

Studies with intact male Sprague-Dawley rats (300g body weight) are illustrated for compounds (1) and (2). Thus, subcutaneous administration in sesame oil of 13mg per kilo per day of compound 5 for 7 days resulted in 30% reduction in weight of the ventral prostate. Furthermore, administration of compound (1) in propylene glycol intraperitoneally at a dosage of 20mg per kilo per day for 7 days resulted in 28% of reduction in weight of the ventral prostate.

| Compound and Dosage | Average Weight of Ventral Prostate |
| --- | --- |
| Controls; 0.2ml sesame oil per rat per day for 7 days, s.c. | 238 mg |
| Compound 5; 13mg/Kg in sesame oil (0.2ml) per rat per day for 7 days, s.c. | 167 mg |
| Controls; 0.2ml propylene glycol per rat per day for 7 days, i.p. | 421 mg |
| Compound 5; 13mg/Kg in propylene glycol (0.2ml) - per rat per day for 7 days, i.p. | 302 mg |

Similarly, compound (2), when administered in propylene glycol intraperitoneally to intact male Sprague-Dawley rats at a dosage of 20mg per kilo for 7 days produced 20% reduction in weight of the ventral prostate and 28% reduction of the dorsal lateral prostate.

The following Chart I illustrates a synthetic route for the preparation of compounds 1(a-c) according to the invention:

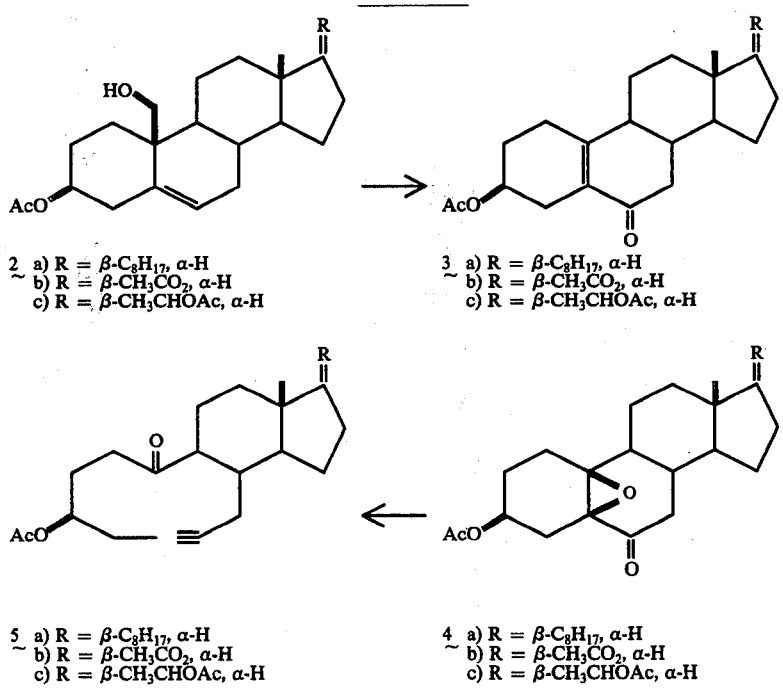

CHART I 2  a) R = β-C$_8$H$_{17}$, α-H
   b) R = β-CH$_3$CO$_2$, α-H
   c) R = β-CH$_3$CHOAc, α-H 3  a) R = β-C$_8$H$_{17}$, α-H
   b) R = β-CH$_3$CO$_2$, α-H
   c) R = β-CH$_3$CHOAc, α-H 5  a) R = β-C$_8$H$_{17}$, α-H
   b) R = β-CH$_3$CO$_2$, α-H
   c) R = β-CH$_3$CHOAc, α-H 4  a) R = β-C$_8$H$_{17}$, α-H
   b) R = β-CH$_3$CO$_2$, α-H
   c) R = β-CH$_3$CHOAc, α-H

-continued
CHART I

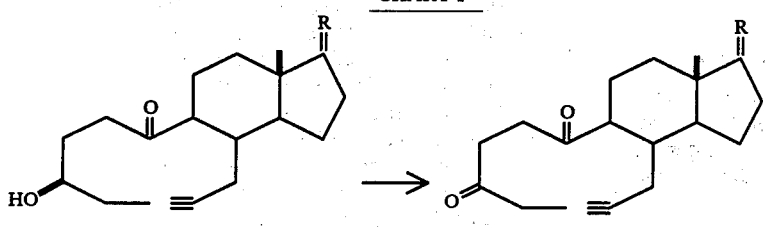

6  a) R = β-C₈H₁₇, α-H
   b) R = β-OH, α-H
   c) R = β-CH₃CHOH, α-H 1  a) R = β-C₈H₁₇, α-H
   b) R = O
   c) R = β-CH₃CO, α-H

The critical part of the process route involves generation of the key $\Delta^{5(10)}$-6-oxo intermediate (3a) with subsequent fragmentation of the derived 5β,10β-oxido-6-ketone (4a) to (5a) by the Tanabe-Eschenmoser[9] procedure. The compound (3a) is prepared by direct conversion of $\Delta^5$-19-hydroxysteroids to $\Delta^{5(10)}$-6-ketones using chromium trioxide-pyridine at 25°. (See U.S. Pat. Nos. 3,159,621 and 3,261,830). This method (4 days at ambient temperature followed by chromatrography on silica gel) gives the $\Delta^{5(10)}$-6-ketone (3a) conveniently in 40% yield. Epoxidation of 3a to give the oxidoketone (4a) is carried out using alkaline hydrogen peroxide, followed by reacetylation at C-3 for easier isolation and characterization.

9. M. Tanabe, D. F. Crowe and R. L. Dehn, Tetrahedron Lett., 3943 (1967); A. Eschenmoser, D. Felix and G. Ohloff, Helv. Chim. Acta, 50, 708, (1967).

The 5β,10β-configuration for 4a is inferred from the negative c.d. curve,[10] as well as from the following evidence:

10. P. Crabbe, ORD and CD in Chemistry and Biochemistry, Academic Press, New York, N.Y., 1972, p. 40.

The known 3β-acetoxy-$\Delta^{5(10)}$-6β-ol (7) of established[11] stereochemistry is converted quantitatively by m-chloroperbenzoic acid to the 5,10-oxido compound (8).

11. P. Morand and M. Kaufman, Canadian J. Chem., 49, 3185 (1971). The well established[12] directive effect of the hydroxyl group in the peracid epoxidation of allylic alcohols indicates the 5β,10β-configuration of the epoxide grouping in 8. Oxidation of 8 with Jones reagent then gives in quantitative yield, the oxidoketone (4a), identical in all respects with 4a prepared by H₂O₂-NaOH epoxidation of the conjugated ketone 3a followed by reacetylation at C-3.
12. P. Chamberlain, M. L. Roberts and G. H. Whitham, J. Chem. Soc., B, 1374 (1970) and reference therein.

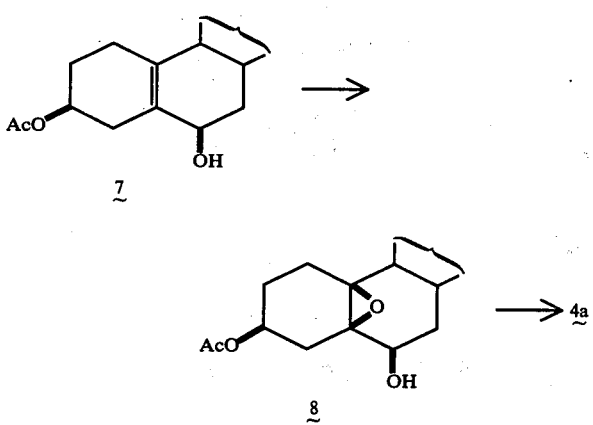

The 5β,10β-oxido-6-ketone 4a is then fragmented to give 5a by the Tanabe-Eschenmoser reaction (p-toluenesulfonylhydrazide in acetic acid-chloroform at room temperature). Spectroscopic and analytical data are consistent with structure 5a while positive evidence for the acetylenic grouping from the Raman spectrum which showed absorption at 2230 cm⁻¹. In addition, catalytic hydrogenation of 5a using Adams catalyst gives the tetrahydro derivative.

The 3β-acetoxy-5,10-secosteroid 5a is then hydrolyzed to the 3β-ol (6a), and oxidation with Jones reagent then affords, in ca. 50% yield, the final product 1a, which gives appropriate spectroscopic and analytical data.

The marked lack of reactivity of the C-10 carbonyl group in 5a is noteworthy. Attempts to prepare the p-toluenesulfonylhydrazone have filed, even under forcing conditions (e.g. p-toluenesulfonylhydrazide and p-toluenesulfonic acid in sulfolanedimethylformamide at 100°). Attempts to generate the oxime, using conditions (hydroxylamine-pyridine, reflux) suitable[13] for hindered 11-oxosteroids have also failed. Furthermore, no reduction of the 10-ketone has been observed under forcing Wolff-Kishner conditions, or by the use of sodium borohydride or lithium aluminum hydride. This lack of reactivity might be due in part to electronic interaction between the acetylene and 10-carbonyl functions. However, this is unlikely to be a major factor, as the tetrahydro compound obtained by catalytic hydrogenation of the acetylenic compound 5a has also proven to be inert to hydrazone-forming reagents. The formation of an intermediate complex would result in severe transannular interactions in the 10-membered ring, and this effect may play a critical role.

13. E. B. Hershberg, E. P. Oliveto and R. Rausser, Chem. and Ind., 1477 (1958).

The sequence of Chart I as outlined above for the cholestane series can be applied in the preparation of the 5,10-secoestryne (1b) and 5,10-seco-19-norpregnyne (1c). It has been observed that the 5β-10β-oxidoketone system (e.g. 4b) can be conveniently prepared by treatment of the corresponding $\Delta^{5(10)}$-6-ketone with m-chloroperbenzoic acid in benzene under reflux. The undesired Baeyer-Villiger reaction does not compete to a major extent, and this procedure gives the crystalline oxidoketone 4b directly in 67% yield without the reacetylation required after the H₂O₂-NaOH procedure.

The 5β-10β-configuration for the oxido compounds 4b and 4c is inferred from their negative c.d. curves, as well as from analogy with the cholestane series. In addition, chromous acetate[14] reduction of 4b gives the 10β-hydroxy-6-ketone 9, which shows a negative c.d. spectrum as expected for a 6-oxosteroid of the 5α,10β-series.

The final products 1b and 1c are obtained by fragmentation of oxidoketones 4b and 4c, followed by hydrolysis of the acetate groupings and oxidation with Jones reagent, as for the cholestane series. It should be noted that hydrolysis of the acetoxy groups in 5 a–c 14. R. Henderson and C. H. Robinson, *J. Org. Chem.*, 37, 565 (1972). with base does not cause epimerization at C-9. Thus, reacetylation of the hydrolyzed products 6 a–c generates, in quantitative yield, unchanged 5 a–c as evidenced by spectroscopic, chromatographic and c.d. measurements.

The following additional examples further illustrate the invention:

EXAMPLE 18

3β-Acetoxy-19-norcholest-5(10)-en-6-one(3a)

3β-acetoxy-19-hydroxycholest-5-ene(15.8g, 0.036 mole) was dissolved in pyridine (100 ml) and stirred with chromium trioxide-pyridine complex (0.30 mole) at ambient temperature for 4 days. The mixture was diluted with EtOEt(1.5 l) and filtered. The ethereal phase was washed successively with 5% NaOH and H$_2$O. The residue obtained by concentration in vacuo was chromatographed on silica gel by elution with 6% EtOAc-CHCl$_3$. Early fractions contained several non-polar compounds followed by (3a) (5.7g, 0.0133 mole, 36%) mp 122°-123° (from MeOH) mass spectrum m/e 428(M+), 400, 382, 368; $\lambda_{max}^{MeOH}$246 nm ($\epsilon$ 11, 430); [$\theta$](MeOH)+2530°(329 nm); $\nu$ max(KBr)1725 (ester C=O), 1660(C=O) 1660cm$^{-1}$(C=C); nmr (C$_6$D$_6$)4.50(m,1,C$\underline{H}$OAc), 2.46(m,2,COCH$_2$), 2.00(s,3,C$\underline{H}_3$CO), 0.85(s,3,18-C$\underline{H}_3$)

Anal. Calcd. for C$_{28}$H$_{44}$O$_3$: C,78.45; H,10.35; Found: C,78.43; H,10.15

EXAMPLE 19

3β-Acetoxy-5β,10β-oxido-19-norcholestan-6-one (4a)

3β-Acetoxy-19-norcholest-5(10)-en-6-one (3a, 235 mg, 0.00055 mole) was dissolved in MeOH-CHCl$_3$ (15 ml: 3ml). At ambient temperature a mixture of 30% H$_2$O$_2$ (1 ml) and 5N NaOH (1 ml) was added. After stirring for 5 hr the reaction mixture was diluted with aqueous NaCl(sat) and extracted with CHCl$_3$. Drying (Na$_2$SO$_4$) and removal of solvent in vacuo left a solid which was acetylated with acetic anhydride-pyridine (18 hr., room temperature). After work up in the usual manner the residue was crystallized from MeOH to give 4a as needles (150 mg, 0.00033 mole, 58%): mp 173°-174°; mass spectrum m/e 444 (M+), 384, 368, 356, 340; $\nu$max 1735 (ester C=O), 1705cm$^{-1}$(c=O); [$\theta$] (CH$_3$OH) — 8894° (307.5nm); nmr 4.62 (m,1,C$\underline{H}$OAc), 2.02 (s,3,C$\underline{H}_3$CO), 0.70 (s,3,18-C$\underline{H}_3$)

Anal. Calcd. for C$_{28}$H$_{44}$O$_4$: C,75.63; H,9.97; Found: C,75.48; H,9.79

EXAMPLE 20

3β-Acetoxy-5β,10β-oxido-19-norcholestan-6-one (4a) from 3β-acetoxy-6β hydroxy-19-norcholest-5(10)-ene (7)

A solution of the Δ$^{5(10)}$-6β-ol$^{11}$(7, 54 mg, 0.00013 mole) and 85% m-chloroperbenzoic acid (54 mg, 0.00027 mole) in CHCl$_3$ (8 ml) was left at ambient temperature for 18 hr. Water was then added, and the CHCl$_3$ phase was washed successively with 10% aqueous Na$_2$SO$_3$ solution, 10% NaHCO$_3$ solution and water, and then was dried (Na$_2$SO$_4$) and evaporated. The residue was crystallized from acetone to give 8, mp 140°-141°; mass spectrum m/e 428 (M-18), 386, 368.

Oxidation of the above product with Jones reagent in acetone at 5° for 15 minutes gave crude 4a as a crystalline product. This material was homogenous by tlc, had mp 173-174° and was identical in all respects (ir, nmr, cd, ms) with a sample of 4a, prepared by H$_2$O$_2$-NaOH epoxidation of the conjugated ketone 3a followed by reacetylation at C-3.

EXAMPLE 21

3β-Acetoxy-5,10-seco-19-norcholest-5-yn-10-one (5a)

3β-Acetoxy-5,10-oxidocholestan-6-one (4a, 666 mg, 0.0015 mole) and p-toluenesulfonylhydrazide (333 mg, 0.0018 mole) were dissolved in 1:1 CHCl$_3$-AcOH (50 ml). After stirring 5 hr at ambient temperature the reaction mixture was diluted with water and CHCl$_3$. The organic phase was washed with water and 5% NaHCO$_3$. Removal of the dried (Na$_2$SO$_4$) solvent in vacuo gave an oil which crystallized from MeOH, giving 5a as plates (471 mg, 0.0011 mole, 73%: mp 105°-106°; mass spectrum m/e 428 (M+), 386, 368, 350; $\nu$max 1730 (ester C=O), 1705cm$^{-1}$(C=O); [$\theta$] (CH$_3$OH) — 2805° (283 nm); nmr 4.80 (m,1,C$\underline{H}$OAc), 2.02 (s,3,C$\underline{H}_3$CO), 0.76 (s,3,18-C$\underline{H}_3$)

Anal. Calcd. for C$_{28}$H$_{44}$O$_3$: C,78.45; H,10.35; O,11.20; Found: C,78.27; H,10.35; O,11.20

EXAMPLE 22

3β-Hydroxy-5,10-seco-19-norcholest-5-yn-10-one (6a)

The acetate (5a) (35 mg, 0.00008 mole) was dissolved in MeOH (7ml) and stirred with anhydrous K$_2$CO$_3$(150 mg) for 2 hr. Filtration and evaporation of the solvent left a solid which was crystallized from hexane to give 6a as needles (30 mg, 0.000078 mole, 97%): mp 153°-154°; mass spectrum m/e 386 (M+), 368, 340; $\nu$max (KBr) 3400 (OH), 1705cm$^{-1}$ (C=O); [$\theta$] (CH$_3$OH) — 2556° (283 nm); nmr 3.84 (m,1CHOH), 0.75 (s,3,18-CH$_3$).

Anal. Calcd. for C$_{26}$H$_{42}$O$_2$: C,80.83; H,10.88; Found: C,80.66; H,10.79

EXAMPLE 23

5,10-Seco-19-norcholest-5-yne-3,10-dione (1a)

3β-Hydroxy-5,10-Seco-19-norcholest-5-yn-10-one (6a, 163 mg, 0.00042 mole) was dissolved in acetone (50 ml) and oxidized with excess Jones reagent for 10 minutes at ambient temperature. The mixture was diluted with H$_2$O and extracted with CHCl$_3$. Drying (Na$_2$SO$_4$) and removal of the solvent in vacuo gave an oil which was crystallized from MeOH-EtOEt to give (1a, 77 mg, 0.0002 mole): mp 94°-96°; mass spectrum m/e 384 (M+), 269, 256, 299; [$\theta$](dioxane)—6696° (287 nm); $\nu$max (KBr) 1705cm$^{-1}$; nmr 0.75 (s,3,18-C$\underline{H}_3$).

Anal. Calcd. for C$_{26}$H$_{40}$O$_2$: C,81.25; H,10.42; Found: C,81.49; H,10.53

EXAMPLE 24

3β-Diacetoxyestr-5(10)-en-6-one (3b)

Compound 3b was prepared in a manner identical with that for (3a) as described above: mp 116°-118°; mass spectrum m/e 374 (M+), 332, 314, 286; $\lambda_{max}^{MeOH}$ 245 nm ($\epsilon$11,078); [$\theta$] (CH$_3$OH) +2372° (330 nm); $\nu$max (KBr) 1730 (ester C=O), 1660 (C=O), 1620 cm$^{-1}$ (C=C); nmr 5.11 (m,1,C$\underline{H}$OAc), 4.66 (m,1,C$\underline{H}$OAc), 2.02 (s,3,C$\underline{H}_3$CO), 2.00 (s,3,C$\underline{H}_3$CO), 0.86 (s,3,18-C$\underline{H}_3$)

Anal. Calcd. for C$_{22}$H$_{30}$O$_5$: C,70.58; H, 8.02; Found: C,70.31; H,8.14

EXAMPLE 25

3β,17β-Diacetoxy-5β,10β-oxidoestran-6-one (4b)

A mixture of 3β,17β-Diacetoxyestr-5(10)-en-6-one (3b, 3.74 g, 0.01 mole) and 85% m-chloroperbenzoic acid (5.74 g, 0.028 mole) was refluxed in benzene (300 ml) for 1 hr. The cooled solution was washed sucessively with water, 5% NaHCO$_3$, water and dried (Na$_2$SO$_4$). The residue crystallized from MeOH, after removal of the solvent in vacuo, to give pure epoxide (4b). Chromatography of the mother liquor on silica gel (elution with 8% EtOAc-CHCl$_3$) gave additional (4b), total yield 2.7 g 0.0067 mole, 67%): mp 245°-247°; mass spectrum m/e 390 (M+), 330, 314, 302, 286; νmax 1725 (ester C=O), 1705 (C=O), 1250 cm$^{-1}$ (ester); [θ] (CH$_3$OH) −8506° (306 nm); nmr (C$_6$D$_6$) 4.60 (m,2,CHOAc), 2.06 (s,3,CH$_3$CO) 2.01 (s,3,CH$_3$CO), 0.84 (s,3,18-CH$_3$)

Anal. Calcd. for C$_{22}$H$_{30}$O$_6$: C,67.67; H,7.74; Found: C,67.65; H,7.66

EXAMPLE 26

3β,17β-Diacetoxy-5β,10β-oxidoestran-6-one (4b) from 3β,6β,17β-Triacetoxyestr-5(10)-ene (10)

To a solution of the triacetate (10, 1.0 g, 0.0026 mole) in acetone (40 ml) at 25° was added Jones reagent (1.2 ml) with swirling. After 10 min, excess reagent was destroyed by dropwise addition of MeOH, and the reaction mixture was diluted with water, and extracted with CHCl$_3$. The CHCl$_3$ extract was washed with water, dried (Na$_2$SO$_4$) and evaporated in vacuo to give a solid residue which was chromatographed on silica gel (elution with CHCl$_3$-EtOAc, 9:1). The first fractions contained starting material (10, 119 mg), and later fractions contained the oxidoketone (4b, 200 mg), mp 247° (from MeOH) identical in all respects (ir, nmr, tlc, ms) with an authentic sample of 4b.

EXAMPLE 27

3β,17β-Diacetoxy-5,10-secoestr-5-yn-10-one (5b)

A mixture of 3β,17β-Diacetoxy-5β,10β-oxidoestran-6-one (4b, 2.0 g, 0.005 mole) and p-toluenesulfonylhydrazide (1,24 g, 0.0067 mole) was stirred for 6 hrs. in 1:1 CHCl$_3$-AcOH (150 ml) at ambient temperature. The CHCl$_3$ extract, after dilution with water, was washed with 5% NaHCO$_3$, water and dried (Na$_2$SO$_4$). Removal of the solvent in vacuo and crystallization of the residue (MeOH) gave 5b as plates (1.7 g, 0.0045 mole, 90%): mp 204°-206°; mass spectrum m/e 374 (M+), 332, 316, 304, 286; max 1724 (C=O), 1250 cm$^{-1}$ (ester); [θ] (CH$_3$OH)-2710° (284 nm); nmr 4.62 (m,2,CHOAc), 2.01 (s,6,CH$_3$CO at C-3 and C-17), 0.88 (s,3,18-CH$_3$)

Anal. Calcd. for C$_{22}$H$_{30}$O$_5$: C,70.56; H,8.08; Found: C,70.70; H,7.94

EXAMPLE 28

3β,17β-Dihydroxy-5,10-secoestr-5-yn-10-one (6b)

The diacetate (5b, 374 mg, 0.001 mole) was stirred at ambient temperature for 3 hr in 3% methanolic KOH (75 ml). Concentration in vacuo after the addition of sat. NaCl (40 ml); extraction with CHCl$_3$, drying (Na$_2$SO$_4$) and removal of the solvent gave the pure diol (6b). Crystallization from hexane-EtOH gave 6b as needles (280 mg, 0.0096 mole, 96%): mp 205°-207°; mass spectrum m/e 290 (M+), 272, 262, 254, 244; νmax (KBr) 3440 (OH), 1725 cm$^{-1}$ (C=O); [θ] (CH$_3$OH) −2744° (283 nm); nmr (d$_6$-DMSO) 4.85 (m,1,CHOH), 4.57 (m,1,CHOH), 0.78 (s,3,18-CH$_3$)

Anal. Calcd. for C$_{18}$H$_{26}$O$_3$: C,74.44; H,9.03; Found: C,74.21; H,8.99

EXAMPLE 29

5,10-Secoestr-5-yne-3,10,17-trione (1b)

The 3β,17β-diol (6b, 186 mg, 0.0006 mole) was dissolved in acetone (40 ml) and oxidized with excess Jones reagent for 5 min at ambient temperature. The reaction was diluted with water and extracted with CHCl$_3$. The residue obtained after removal of solvent was crystallized from petroleum ether —CHCl$_3$ to give 1b as plates (98 mg, 0.00034 mole, 53%): mp 163°-166°; mass spectrum m/e 286 (M+), 271, 258, 243, 230, 215; νmax 1730 (C=O) 1730cm$^{-1}$ (C=O); [θ] (MeOH) +4607° (305 nm), −3016° (277 nm), +1426° (248 nm); nmr 0.93 (s,3,18-CH$_3$)

Anal. Calcd. for C$_{18}$H$_{33}$O$_3$: C,75.49; H,7.74; O,16.77; Found: C,75.25; H,7.61; O,16.67

EXAMPLE 30

3β,10β,17β-Trihydroxy-5α-estran-6-one 3β,17β-Diacetate (9)

A mixture of 3β,17β-Diacetoxy-5β,10β-oxidoestran-6-one (4b, 800 mg, 0.0021 mole) and chromous acetate[15] (3.4 g, ca. 0.2 mole) was stirred at ambient temperature for 24 hr in 90% aqueous acetone (150 ml) under an atmosphere of argon. The reaction mixture was diluted with water and extracted with CHCl$_3$. The extract was washed with H$_2$O, dried (Na$_2$SO$_4$) and evaporated in vacuo. The residue was chromatographed on silica gel (elution with 11% EtOAc in CHCl$_3$). Early fractions gave unchanged oxidoketone (4b) followed by enone (3b). The most polar fractions gave the desired β-hydroxyketone (9, 75 mg, 0.00019 mole, 9%) mp 196°-199°; mass spectrum m/e 392 (M+), 376, 349, 314, 304, 272; νmax (KBr) 3480 (OH), 1735 cm$^{-1}$(C=O); [θ] (CH$_3$OH) −5078° (288 nm).

Calcd. for C$_{22}$H$_{32}$O$_6$: m/e 392.21900; Found: m/e 392.22510

EXAMPLE 31

3β,20β-Diacetoxy-19-norpregn-5(10)-en-6-one (3c)

Compound 3c was prepared in a manner identical with that for (3a) as described above: mp 126°-127° (from acetone-light petroleum); mass spectrum m/e 402 (M+), 342, 300, 254; λ$_{max}^{MeOH}$ 247 nm (ϵ10,435); [θ] (MeOH) +2747° (330 nm); νmax (CHCl$_3$) 1725 (ester C=O), 1660 (C=O), 1625 cm$^{-1}$ (C=C); nmr 4.82 (m,2,CHOAc), 2.0 (s,6,CH$_3$CO), 0.65 (s,3,18-CH$_3$)

Anal. Calcd. for C$_{24}$H$_{34}$O$_5$: C,71.61; H,8.51; Found: C,71.60; H,8.26

EXAMPLE 32

3β,20β-Diacetoxy-5β,10β-oxidopregnan-6-one (4c)

3β,20β-Diacetoxy-19-norpregn-5,(10)-en-6-one (3c, 250 mg, 0.00062 mole) was dissolved in MeOH (18 ml) containing 30% H$_2$O$_2$ (1.25 ml) and 5N NaOH (1.25 ml). After stirring 3 hr at ambient temperature the reaction was diluted with brine and extracted with CHCl$_3$. The extract was washed with 5% NaHSO$_3$, dried with (Na$_2$SO$_4$) and removed in vacuo. The residue was acetylated (pyridine-acetic anhydride) and worked up in the usual manner. Crystallization from hexane-EtOH afforded the pure oxide (4c, 186 mg, 0.00045, 72%): mp 143°-145°; mass spectrum m/e 418 (M+), 360, 358, 342, 340, 330, 298, 270; νmax 1740 (ester C=O), 1700 cm$^{-1}$ (C=O); [θ] (CH$_3$OH) −9000° (307 nm); nmr 4.68

(m,2,C$\underline{H}$OAc), 2.00 (s,6,C$\underline{H}_3$CO), 1.14 (d,3,J=6gHz, 21-C$\underline{H}_3$), 0.68 (s,3,18-C$\underline{H}_3$)

Anal. Calcd. for $C_{24}H_{34}O_6$: C,68.87; H,8.19; Found: C,68.71; H,8.11

EXAMPLE 33

3β,20β-Diacetoxy-5,10-seco-19-norpregn-5-yn-10-one (5c)

A mixture of 3β,20β-Diacetoxy-5β,10β-oxidopregnan-6-one (4c, 150 mg, 0.00036 mole) and p-toluenesulfonylhydrazide (78 mg, 0.0043 mole) was stirred 6 hr. at ambient temperature in 1:1 $CHCl_3$—AcOH (15 ml). The reaction mixture was diluted and extracted with $CHCl_3$. The extract was washed successively with $H_2O$, 5% $NaHCO_3$ and $H_2O$. The residue obtained after drying ($Na_2SO_4$) and removal of solvent was crystallized from hexane-acetone to give 5c as plates (105 mg, 0.00026 mole, 72%): mp 119°-120°; mass spectrum m/e 418 (M+), 360, 358, 342, 340, 330, 298, 270; νmax 1735 cm$^{-1}$(C=O); [θ] (CH$_3$OH) −2098° (283 nm); nmr 4.80 (m,2,C$\underline{H}$OAc), 2.05 (s,3,C$\underline{H}_3$CO), 2.00 (s,3,C$\underline{H}_3$CO), 1.15 (d,3,J=6Hz,21-C$\underline{H}_3$),0.80 (s,3,18-C$\underline{H}_3$)

Anal. Calcd. for $C_{24}H_{34}O_6$: C,71.61; H,8.51; Found: C,71.53; H,8.64

EXAMPLE 34

3β,20β-Dihydroxy-5,10-seco-19-norpregn-5-yn-10-one (6c)

The diacetate (5c, 30 mg, 0.000075 mole) was refluxed in 3% methanolic KOH (7 ml) for 2 hr. The reaction was diluted with brine, extracted with $CHCl_3$, dried ($Na_2SO_4$) and concentrated in vacuo to give 6c, (23 mg, 0.00072 mole, 96%): mp 180°-182° (from hexane-EtOH) mass spectrum m/e 318 (M+), 300, 285, 282, 272; νmax (KBr) 3500 (1720 cm$^{-1}$(C=O); [θ] (MeOH) −3067° (283 nm); nmr 3.74 (m,2,C$\underline{H}$OH), 1.09 (d,3,21-C$\underline{H}_3$), 0.83 (s,3,18-C$\underline{H}_3$)

Anal. Calcd. for $C_{20}H_{30}O_3$: C,75.43; H,9.50; Found: C,75.38; H,9.50

EXAMPLE 35

5,10-Seco-19-norpregn-5-ny-3,10,20-trione (1c)

3β,20β-Dihydroxy-5,10-seco-19-norpregn-5-yn-10-one (6c, 140 mg, 0.00044 mole) was dissolved in acetone (50 ml). Excess Jones reagent was added and the mixture was stirred 5 min at ambient temperature. The residue obtained after dilution with water and extraction with $CHCl_3$ was crystallized from hexane-EtOH to give 1c (75 mg, 0.00024, 54%): mp 156°-159°; mass spectrum m/e 314 (M+), 286, 271; νmax (KBr) 1705 cm$^{-1}$; [θ] (dioxane) +4737° (301 nm); nmr 2.14 (s,3,21-C$\underline{H}_3$CO), 0.75 (s,3,18-C$\underline{H}_3$)

Anal. Calcd. for $C_{20}H_{26}O_4$: C,76.40; H,8.34; O,15.66; Found: C,76.22; H,8.21; O,15.97

In the preceding examples, it should be noted that melting points were determined on a Kofler hot stage and are uncorrected. Nmr spectra were determined on Varian HA-100 or Perkin-Elmer R-12B spectrometers for $CDCl_3$ solutions, unless otherwise stated, with TMS as internal standard. Chemical shifts are expressed as values (TMS = O) with signal multiplicities shown as s, singlet; d, doublet; t, triplet; m, multiplet. Infrared spectra were obtained on Perkin-Elmer 137 or 521 spectrometers (in $CHCl_3$ solution unless otherwise stated). Ultraviolet spectra were measured on a Cary 15 spectrophotometer. Mass spectra were determined on CEC-21-110 or Dupont 21-491 spectrometers. Circular dichroism measurements were made using a Cary 60 instrument and are expressed as molar ellipticities. All chromatographic separations were performed on Woelm dry column silica gal or alumina. Analytical thin-layer plates (0.25 mm) were obtained from Analtech, Inc., Newark, Del. High pressure liquid chromatographic separations were performed on a Waters Associates Model 600 instrument equipped with a Model 660 solvent programmer.

The following data illustrates the inhibiting effect of estryne and pregnyne on $Δ^5$-3-ketosteroid isomerase (EC 5.3.3.1) as evidenced by a depression of the wet weight of the sex accessory tissue in the mature male rat treated with the estryne and pregnyne.

The animals used in these tests were male Sprague-Dawley rate (250–300 g); female, 21 day old CF-1 mice (12–15 g); and hypophysectomized male Sprague-Dawley rats (200–250 g). The animals were housed in a temperature controlled room under a constant lighting schedule and maintained on a diet of Charles River Rat Formula and water ad libitum. The diet of the hypophysectomized animals were supplemented with oranges.

STUDY IN INTACT RATS

A. Male rats were used to assess the effect of estryne on endogenous androgen biosynthesis at varying doses (1–20 mg/kg body weight). The estryne was administered interperitoneally in propylene glycol (0.2 ml) daily for seven days. On the eighth day the animals were sacrificed and the ventral prostate, dorsal lateral prostate, seminal vesicles, testes, kidneys, and adrenals were removed and weighed. Samples of each tissue were preserved in 10% buffered formalin for histological examination.

B. Male rats were treated with 19-norpregnyne by a regimen exactly as described for the estryne.

C. To assess the effect of body weight decrease on the wet weight of sex accessory tissue, animals were deprived of food while receiving water ad libitum until they lost 20% body weight relative to controls, and were sacrificed on the appropriate day for organ weight determination.

STUDY IN CASTRATE RATS

To determine if the estryne competes with testosterone at the target tissue rats were orchiectomized under ether anesthesia via the scrotal route 10 days prior to treatment. Testosterone propionate 0.3 mg (0.2 ml sesame oil) was administered daily for 7 days subcutaneously. Estryne 12 mg/kg (0.2 ml propylene glycol) was given daily for 7 days interperitioneally. Control groups received either testosterone propionate (0.3 mg) or carrier oil daily for 7 days. The animals were sacrificed on the eighth day and the organs were weighed.

STUDY IN HYPOPHYSECTOMIZED RATS

In order to assess the action of the estryne in the presence of exogenous stimulation of androgen synthesis, hypophysectomized male rats received estryne 3.0 mg (0.2 ml sesame oil) sc and/or human chorionic gonadotropin 2 units and 4 units (0.9% saline) sc daily for 7 days. Sacrifice and weighing of the organs was performed on the eighth day.

STUDY OF ESTROGENIC ACTIVITY

Estrogenic activity was determined in 21 day old CF-1 female mice receiving either estryne (1–100μg) or estradiol (4 mg – 192 mg) b.i.d. × 3 days in 10% dioxanesesame oil (0.05 ml) sc. On the fourth day the uteri were removed and weighed.

STUDY OF THE BINDING TO THE PROSTATE ANDROGEN BINDING PROTEIN

The binding to the cytosol androgen receptor was determined by the procedure of Fang (5) with modification. Thus, 400 mg of freshly minced ventral prostate tissue obtained from rats castrated 24 hours before sacrifice was incubated at 37° for one hour in 5 ml of TM buffer (50 mM tris, 3 mM Mg $Cl_2$, 0.3 M sucrose) pH 7.4 containing 14 $\mu$Ci of $^3$H-dihydrotestosterone (85 Ci/mM, New England Nuclear Corp., Boston, Mass.), together with estryne or pregnyne (2 × 10$^{-6}$M) under an atmosphere of 95% oxygen and 5% carbon dioxide. Cyproterone acetate and unlabelled dihydrotestosterone were used as steroidal controls. Following incubation the tissue was washed three times with cold TM (5 ml) and the nuclei were isolated by the method of Coffey et al. (Coffey, D. S. Shimazaki, J. and Williams-Ashman, H. G., Arch. Biochem. Biophys., 124, 184 (1968). The amount of radioactivity in the nuclei is expressed as observed counts per minute per 100 $\mu$g DNA. The amount of DNA was assayed by the Burton diphenylamine method, with calf thymus DNA as the reference (see Burton, K., Methods in Enzymology, vol. 12B, 163, L. Crossman and K. Maldane (eds.), Academic Press, New York, 1968).

RESULTS

Since growth inhibition or cell death of the sex accessory tissue can result from multiple mechanisms, it was necessary to study the mode of action of the estryne and 19-nor-pregnyne. The following modes of action were considered: (a) direct competition with testosterone and dihydrotestosterone for the androgen nuclear binding protein of the ventral prostate, (b) suppression of luteinizing hormone production by action on the hypothalamus or pituitary, (c) direct estrogenic action, (d) inhibition of androgen biosynthesis.

STUDIES IN INTACT RATS

A. The acetylenic steroid analogue 5,10-secoestr-5-yne-3,10,17-trione (estryne) depresses the wet weight of both the ventral and dorsal-lateral prostate in short term treatment (7 days). Only a modest decrease is observed for the seminal vesicles, and no effect on the testes, or kidney, or adrenal for the same treatment. The estryne caused a decrease (25–30%) in the wet weight of both the ventral and dorsal-lateral prostate at a daily dose (7 days) of 20mg/kg/body weight. The effect on the prostatic weight was dose dependent for the estryne. (Table 1).

B. The 19-norpregnyne analogue decreased the weight of the ventral and dorsal-lateral prostate by the same percent as the estryne at a dose of 20mg/kg/body weight for 7 days. The weight decrease was also dose dependent (Table 2).

C. Both acetylenic steroids were equally effective at a given dose administered intraperitoneally or subcutaneously. At a dose of 20mg/kg/body weight for 7 days by the IP route a 20% decrease in body weight relative to controls occurred. This loss was not observed for subcutaneous injection or lower doses. In order to access the possible effect of weight loss on the prostate, animals were deprived of food until they had lost 20% body weight relative to controls. No significant change in prostatic weight was observed.

STUDY IN CASTRATE RATS

Animals castrated ten days prior to treatment received both estryne (12mg/kg weight) and testosterone propionate (0.3mg) daily for seven days. No significant depression of prostatic weight was observed. This suggests that the estryne is not blocking the action of androgen at the target tissue by preventing dihydrotestosterone from entering the nucleus.

STUDY IN HYPOPHYSECTOMIZED RATS

Since the estryne does not appear to inhibit the action of androgens at the target tissue in vivo it was necessary to determine if it could antagonize the effect of human chorionic gonadotropin (HGG) which stimulates androgen biosynthesis in the testes of hypophysectomized rats. The wet weight of the ventral prostate was decreased (20–25%) in hypophysectomized animal receiving estryne (12mg/kg/body weight) and HGG (2 units) as compared to controls receiving just HGG (2 units). The effect was less pronounced at higher doses of HGG.

ESTROGENIC ACTIVITY

Due to the potency of estrogens and their marked effect on androgen biosynthesis via the gonadal-pituitary axis the estryne was assayed for estrogenic activity. Thus, immature female mice received estryne at doses up to a maximum of 100 $\mu$g total dose over three days, and the wet weight of the uteri were determined. A 100 $\mu$g total dose, the estryne showed no stimulation of the immature uterus whereas a dose as low as 0.67 $\mu$g of 17$\beta$-estradiol gave a positive response, with maximum stimulation at about 8 $\mu$g using the same dosage schedule as for the estryne.

STUDY OF BINDING TO THE PROSTATIC ANDROGEN RECEPTOR

A. Incubation of estryne (2 × 10$^{-6}$M) with rat ventral prostate mices inhibited the nuclear uptake of $^3$H-dihydrohydrotestosterone (2 × 10$^{-9}$M, 85 Ci/mM) by approximately 50% as determined by the radioactivity present in the isolated nuclei (Table 3).

B. Interestingly incubation of 19-norpregnyne with ventral prostate minces as above showed no inhibition of androgen uptake by the nuclei (Table 3).

Table 1

TREATMENT OF MATURE INTACT RATS WITH ESTRYNE FOR SEVEN DAYS

| Daily Dose | Ventral Prostate | Dorsal Lateral Prostate | Seminal Vesicles | Adrenal | Testis | Kidney |
|---|---|---|---|---|---|---|
| | (mg ± Sem) | | | | | |
| Intact Control | 421 ± 15 | 244 ± 12 | 394 ± 12 | 27 ± 2 | 1650 ± 38 | 1260 ± 63 |
| Castrate Control | 76 ± 7 | 111 ± 9 | 249 ± 20 | 28 ± 1 | — | 1220 ± 33 |
| 1 mg/kg | 435 ± 23 | 212 ± 19 | 380 ± 18 | 28 ± 2 | 1650 ± 60 | 1320 ± 68 |
| 5 mg/kg | 385 ± 8 | 195 ± 8 | 368 ± 16 | 26 ± 2 | 1590 ± 54 | 1090 ± 39 |
| 10 mg/kg | 364 ± 25 | 188 ± 6 | 387 ± 14 | 30 ± 2 | 1580 ± 59 | 1150 ± 42 |

Table 1-continued
TREATMENT OF MATURE INTACT RATS WITH ESTRYNE FOR SEVEN DAYS

| Daily Dose | Ventral Prostate | Dorsal Lateral Prostate | Seminal Vesicles | Adrenal | Testis | Kidney |
|---|---|---|---|---|---|---|
| 20 mg/kg | 302 ± 28 | 177 ± 15 | 309 ± 23 | 30 ± 3 | 1420 ± 64 | 1040 ± 35 |

Table 2
TREATMENT OF MATURE INTACT RATS WITH PREGNYNE FOR SEVEN DAYS

| Daily Dose | Ventral Prostate | Dorsal Lateral Prostate | Seminal Vesicles | Adrenal | Testis | Kidney |
|---|---|---|---|---|---|---|
| | (mg ± Sem) | | | | | |
| Control | 482±24 | 252±14 | 470±26 | 28±2 | 1580±23 | 1410±38 |
| 1 mg/kg | 405±18 | 205±14 | 423±21 | 22±2 | 1530±68 | 1360±48 |
| 5 mg/kg | 402±27 | 208±11 | 384±17 | 25±2 | 1510±44 | 1370±42 |
| 10 mg/kg | 386±20 | 182±19 | 390±14 | 26±1 | 1530±53 | 1310±60 |
| 20 mg/kg | 360±21 | 180±14 | 380±9 | 31±2 | 1480±63 | 1360±43 |

Table 3
Inhibition of Nuclear Uptake of $^3$H-Dihydrolestosterone (DHT) by Estryne and Pregnyne in the Rat Ventral Prostate

| Steroids | Conc (M) | μg DNA/ml | CPM/100 μg DNA | % Control |
|---|---|---|---|---|
| $^3$H-DHT (Control) | $2 \times 10^{-9}$ | 237 | 8,471 | 100 |
| DHT | $2 \times 10^{-6}$ | 255 | 117 | 1.4 |
| $^3$H-DHT | $2 \times 10^{-9}$ | | | |
| Cp - Ac* | $2 \times 10^{-6}$ | 196 | 941 | 11.1 |
| $^3$H-DHT | $2 \times 10^{-9}$ | | | |
| Estryne | $2 \times 10^{-6}$ | 197 | 4,771 | 56 |
| $^3$H-DHT | $2 \times 10^{-9}$ | | | |
| Pregnyne | $2 \times 10^{-6}$ | 230 | 11,636 | 137 |
| $^3$H-DHT | $2 \times 10^{-9}$ | | | |

*Cyproterone Acetate

As noted above, the acetylenic compounds of the invention, e.g. estryne and pregnyne, are converted into the corresponding conjugated allenic ketones which then react irreversibly with the enzyme. These allenic ketones are also novel and constitute an important embodiment of the invention. The allenic ketones derived from estryne are 6β(H)-5,10-secoestra-4,5-diene-3,10,17-trione and 6α(H)-5,10-secoestra-4,5-diene-3,10,17-trione. These allenic ketones have been tested as inhibitors of isomerase and have been found effective in this regard. Under pseudo first order conditions (isomerase, 4.80 μM; allenic ketone, 200 μM; 1 mM phosphate buffer, pH = 7, 6β(H)-5,10-secoestra-4,5-diene-3,10,17-trione is partially converted to the 6α isomer and a half life of 540 sec for loss of enzyme activity was observed. Likewise the 6α allenic compound was partially converted to the β-isomer and gave a half life of 660 sec for loss of enzyme activity. The allenic ketones derived from pregnyne give similar results.

The following examples further illustrate preparation of the allenic steroids of the invention and their utility.

EXAMPLE 36
5,10-Seco-19-norpregna-4,5-diene-3,10,20trione 5,10-seco-19-norpregna-5-yne-3,10,20-trione (200mg, 0.64 mmol) and triethylamine (363mg, 3.59 mmol) were stirred in dioxane (20ml) at room temperature for 3 hr. The solvent and base were removed under oil pump vacuum and the residue chromatographed on dry column silica gel with a 5:1 hexane/acetone mixture as eluent. High pressure, liquid chromatography was used to analyze the column fractions. After combination of fractions there resulted, 39mg (20%) of 6β(H)-5,10-seco-19-norpregna-4,5-diene-3,10,20-trione, mp 122°-124°, $v_{max}^{CHCl_3}$ 1940, 1700, 1665 cm$^{-1}$. An additional mixture (138mg; 69%) which contained the 6β(H)- and 6α(H)-allenes in the ratio 85:15 was also obtained. A portion of this mixture was subjected to HPLC, giving 6α(H)-5,10-seco-19-norpregna-4,5-diene-3,10,20-trione, $v_{max}^{CHCl_3}$ 1940, 1700 and 1665 cm$^{-1}$.

EXAMPLE 37
5,10-Secoestra-4,5-diene-3,10,17-trione 5,10-secoestr-5-yne-3,10,17-trione (200mg, 0.70 mmol) and triethylamine (363mg, 3.59 mmol) were stirred in dioxane (20ml) at room temperature for 3 hr. The solvent and base were removed under aspirator vacuum on a rotary evaporator and the residue chromatographed on dry column silica gel with a 5:1 hexane/acetone mixture as eluent. High pressure liquid chromatography was used to analyze the column fractions. After combination of fractions, 79mg (39%) of 6β(H)-5,10-secoestra-4,5-diene-3,10,17-trione was obtained, mp 144°, $v_{max}^{CHCl_3}$ 1945, 1735, 1710 and 1680 cm$^{-1}$. An additional mixture (80mg, 40%) which contained the 6β(H)- and 6α(H)- allenes in a 76:24 ratio was also obtained. A portion of this mixture was subjected to HPLC, giving 6α(H)-5,10-seco-19-norestra-4,5-diene-3,10,17-trione, $v_{max}^{CHCl_3}$ 1965, 1740, 1710, 1675 cm$^{-1}$.

EXAMPLE 38
Effects of 6β(H)-5,10-Seco-19-norestra-4,5-diene-3,10,17-trione on intact male Sprague-Dawley rats.

The compound (0.6mg) dissolved in propylene glycol (0.2ml) was administered daily for 7 days by the intraperitoneal route. The experimental group and control group each comprised 5 animals, and weights of animals as well the wet tissue weights of ventral prostate and dorsal lateral prostrate are averaged for each group.

| | Wt. of Animals | Wt. of Ventral Prostate | Wt. of Dorsal Lateral Prostate |
|---|---|---|---|
| Experimental Group | 382 g. | 488 mg. | 235 mg. |
| Control Group | 388 g. | 574 mg. | 299 mg. |

It will be appreciated that various modifications may be made in the invention described herein. Hence the scope of the invention is defined by the following claims wherein:

I claim:

1. A 5,10-secosteroid of the formula:

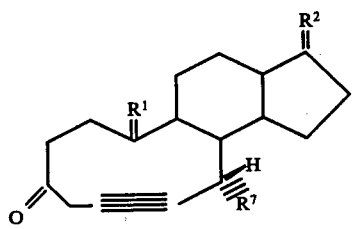

wherein $R^1$ is $CH_2=$, $O=$ or

$R^2$ is $O=$, (where $R^3$ is H or lower alkanoyl);

$$\text{CH}_3\text{CO} \quad ; \quad \text{CH}_3\text{CO} \quad ; \quad \text{CH}_3\text{CO}$$

(where $R^4$ is H or lower alkanoyl);

(where $R^5$ is lower alkyl) or (where $R^6$ is H, lower alkyl or Cl); and $R^7$ is H or $CH_3$.

2. 5,10-secoestr-5-yne-3,10,17-trione.
3. 5,10-seco-19-nor-pregn-5-yne-3,10,20-trione.

* * * * *

UNITED STATES PATENT OFFICE
CERTIFICATE OF CORRECTION

Patent No. 4,059,630   Dated November 22, 1977

Inventor(s) Cecil H. Robinson

It is certified that error appears in the above-identified patent and that said Letters Patent are hereby corrected as shown below:

The formula at the beginning of claim 1 should read:

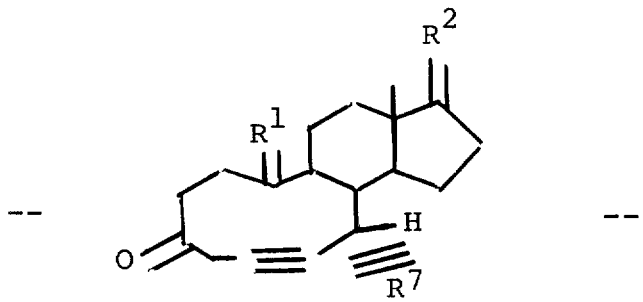

Signed and Sealed this

Twenty-second Day of August 1978

[SEAL]

Attest:

RUTH C. MASON
Attesting Officer

DONALD W. BANNER
Commissioner of Patents and Trademarks